United States Patent [19]
Schwarz et al.

[11] Patent Number: 5,965,817
[45] Date of Patent: Oct. 12, 1999

[54] TEMPERATURE COMPENSATION OF RESONANT FREQUENCY MEASUREMENTS FOR THE EFFECTS OF TEMPERATURE VARIATIONS

[75] Inventors: James J. Schwarz; David E. Thomas; Ronald Karaskiewicz, all of Albuquerque, N.Mex.

[73] Assignee: Quasar International, Inc., Albuquerque, N.Mex.

[21] Appl. No.: 09/123,524

[22] Filed: Jul. 28, 1998

[51] Int. Cl.[6] ........................................ G01H 1/00
[52] U.S. Cl. .................. 73/579; 73/602; 73/766
[58] Field of Search .................. 73/579, 12.01, 73/763, 765, 766, 1.82, 602; 374/117

[56] References Cited

U.S. PATENT DOCUMENTS

| | | | |
|---|---|---|---|
| H1744 | 8/1998 | Clayton et al. | 374/117 |
| 4,535,638 | 8/1985 | EerNisse et al. | 374/117 |
| 4,872,765 | 10/1989 | Schodowski | 374/117 |
| 4,976,148 | 12/1990 | Migliori et al. | |
| 5,062,296 | 11/1991 | Migliori | |
| 5,355,731 | 10/1994 | Dixon et al. | |
| 5,408,880 | 4/1995 | Rhodes et al. | |
| 5,425,272 | 6/1995 | Rhodes et al. | |
| 5,495,763 | 3/1996 | Rhodes et al. | |
| 5,631,423 | 5/1997 | Rhodes. | |
| 5,641,905 | 6/1997 | Schwarz et al. | |
| 5,780,713 | 7/1998 | Ruby | 73/1.82 |

*Primary Examiner*—Hezron Williams
*Assistant Examiner*—Thuy Vinh Tran
*Attorney, Agent, or Firm*—Snider & Chao, LLP; Ronald R. Snider

[57] ABSTRACT

A method for temperature compensation of resonant frequency measurements of parts uses Temperature Functions which are mathematical relationships between measured resonant frequencies and temperature. The Temperature Function is used to adjust frequencies measured at any temperature to a resonant frequency at a pre-determined reference temperature. The temperature of a surrogate part or specimen can be measured to eliminate the need to touch a part being tested where the surrogate part has essentially the same dimensions and material properties and is positioned and mounted such that its temperature is essentially the same as the part being tested. The temperature function may be in the form of $$f_r = f_m * (1 + (T_m - T_r)/C)$$

where $f_r$ is the resonant frequency compensated to the reference temperature, $f_m$ is the measured resonant frequency, $T_m$ is the measured temperature and $T_r$ is the reference temperature.

17 Claims, 1 Drawing Sheet

TEMPERATURE COMPENSATION OF RESONANT FREQUENCY MEASUREMENTS FOR THE EFFECTS OF TEMPERATURE VARIATIONS

BACKGROUND

1. Field of the Invention

This invention relates in general to a resonant testing method and, more particularly to use of temperature compensation of measurements made in a variable temperature location such as a manufacturing operation. Temperatures may vary within a day, or especially, as a part cools after processing. Temperature compensation may be required whenever resonantfrequencies are precisely measured. In particular when resonant ultrasound spectroscopy is used, as illustrated in U.S. Pat. Nos. 5,062,296; 5,408,880; 5,631,423; 5,641,905; 5,425,272; and 5,495,763, temperature compensation may be desired.

2. The Prior Art

Testing of objects by use of sound (including ultrasound) and vibrations is well known. The prior art is extensive and encompasses many types of non-destructive testing. Resonant sound and ultrasound have been used for testing purposes as described in U.S. Pat. Nos. 5,062,296; 4,976,148; and 5,355,731 which are incorporated herein by reference except for their incorporation by reference of other information.

Resonant frequencies of any stiff object, such as a manufactured part or a test specimen, made of metal or ceramic, are fundamentally determined by its dimensions and elastic constants. This observation has been used since the 19th century to detect the presence of defects. For example, railroad engineers are said to have struck wheels and determined the presence of a crack by the change in the audible resonant tone (resonance). The resonance of a cracked wheel has a distinctly lower frequency than that of a good wheel. Since the 1950s, commercial instruments have been available that use this phenomena to provide an impulse to a part and measure the resonant frequency response. These instruments have been used to detect defects in manufactured parts and to measure the elastic constants of test specimens. Generally their accuracy is on the order of 1%, so that they cannot detect the effects of temperature variations on the resonant frequencies. Their relatively poor accuracy also limits their ability to detect small defects.

In the 1980s, Resonant Ultrasound Spectroscopy (RUS—U.S. Pat. No. 5,062,296) was developed and later applied to defect detection and measurement of elastic constants. RUS instruments can make measurements to an accuracy of 0.01%. At this accuracy the effects of temperature can be noticed. This allows detection of much smaller defects, but it also means that the temperature variations can mask the effects of the small defects or small changes in elastic constants. U.S. Pat. Nos. 5,631,423; 5,408,880; 5,495,763; 5,641,905; and 5,425,272 are examples of this method and apparatus. Each of these patents is incorporated by reference except for their incorporation by reference of other material.

SUMMARY OF THE INVENTION

The resonant frequencies vary with the temperature of the part. This temperature variation is relatively small, on the order of—0.015% per degree centigrade for a steel part. So, if the defects are relatively large, or if the accuracy of the frequency measurement instrument is low (say, on the order of 1%), then the effects of temperature are not noticed. Such relatively low accuracy is characteristic of most prior art resonance measurement instruments.

A solution to the problem of temperature induced measurement shift is to hold part temperatures constant. However, this is generally not feasible in a manufacturing facility. The manufacturing environment is not always controlled and the parts may be tested while they are still cooling from the manufacturing process. This invention provides a method for compensating the resonant frequencies measured at any temperature back to a reference temperature. The defect detection techniques disclosed in other patents (for example, relative frequency shifts—U.S. Pat. No. 5,425,272) can be applied based on measurements made at the reference temperature.

This invention provides a method for compensating resonant frequency measurements for the effects of variation in temperature of a measured object comprising the steps of: measuring the frequency of selected resonances of a manufactured part or test specimen at a reference temperature; heating or cooling the part or specimen to another temperature and measuring the new temperature; measuring the frequency of the same resonances at the new temperature; repeating the measurements of frequency and temperature for several temperatures; determining a temperature function which is a mathematical relationship between each resonant frequency and temperature; and using the temperature function to adjust the frequencies measured (fm) at any temperature (Tm) to the frequency (fr) at the reference temperature (Tr). The temperature function for a measured object may be determined by averaging temperature functions for several selected resonances. The temperature of the part or test specimen may be periodically read by a sensor and the part temperature is then input to the temperature function to compensate the part or specimen being tested for temperature change. A temperature sensor may directly contact the part or specimen before the frequency is measured. The temperature may also be remotely sensed with an infrared sensor. Alternately, the temperature of a surrogate part or specimen may be measured to eliminate a need to touch a part or test specimen being tested, wherein said surrogate part or specimen is of the same type and has essentially the same dimensions and material properties as the part or test specimen being tested and is positioned and mounted such that its temperature is essentially the same as the part or test specimen being tested.

The temperature function may be of the form: $f_r = f_m * (1 + (T_m - T_r)/C)$ where $f_r$ is the resonant frequency compensated to the reference temperature, $f_m$ is the measured resonant frequency, $T_m$ is the measured temperature and $T_r$ is the reference temperature. The temperature function may be of the general form $f_r = F(f_m, T_m, T_r)$ where $f_r$ is the resonant frequency compensated to the reference temperature, $f_m$ is the measured resonant frequency, $T_m$ is the measured temperature and $T_r$ is the reference temperature and F is the mathematical notation for "any function of". The method of temperature compensated frequency measurement may apply a frequency to a part, measure the response and then step to a next frequency across a predefined frequency.

DETAILED DESCRIPTION

Figure 1:
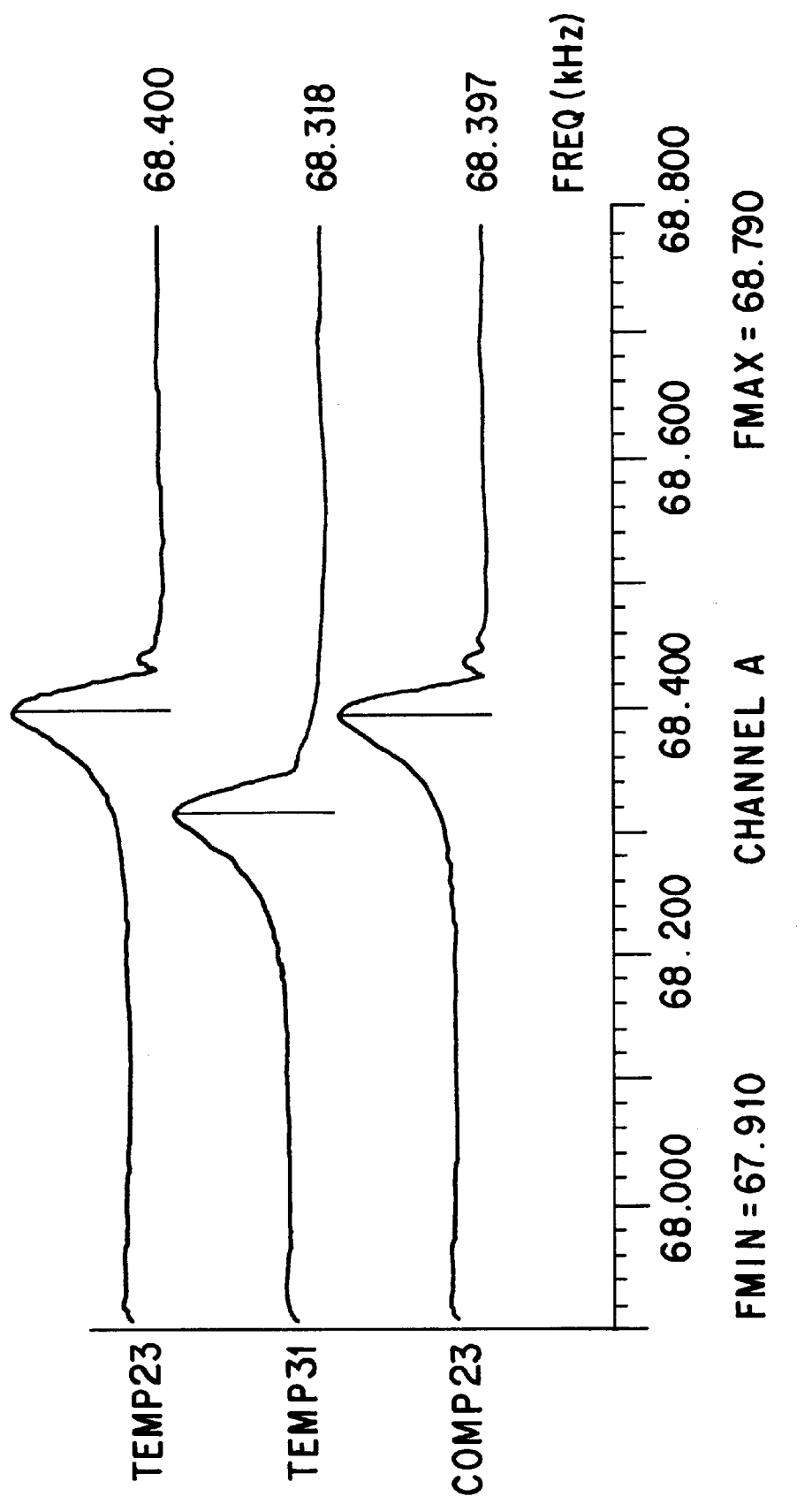
FIG. 1 shows a first trace (temp 23) at a reference temperature of 23° centigrade, a second trace (temp 31) which shows a shift in frequency produced by a temperature change and a third trace (comp 23) which shows second trace (temp 31) compensated back to the temperature at which the first trace (temp 23) was measured.

It is well known that the resonant frequencies of an object vary with temperature. When a resonant technique is used to detect defects or measure elastic constants, the temperature variations can mask smaller variations in the object's resonance pattern and therefore they can represent a fundamental limitation on the use of resonance techniques. This limitation can be overcome by compensating the measured frequencies to adjust them to the frequency that would have been measured at a reference temperature. Fortunately, this can be readily accomplished by measuring the relationship between frequency and temperature for a sample of a given part or specimen and computing a temperature function. Then, when the frequency and temperature of another part are measured, the temperature function can be applied to the data so that any methods used for detecting defects or inferring material properties at a constant temperature, can be used for variable temperatures. This frequency compensation must be accomplished in real time, because the part's temperature is varying. It must be fast and rugged so that it can be implemented in a factory environment.

EXAMPLE

The first step is to determine the temperature function for the part or specimen of interest. This simply requires selecting a set of resonances, and measuring the resonant frequency at several temperatures. The part can be either heated or cooled and the temperature can be measured at several points as it returns to the reference temperature. The resonant frequency can be measured using RUS techniques or any other appropriate instrument. The temperature of the part can be measured using a sensor that contacts the object, such as a thermocouple, or a remote sensor, such as an infrared probe. The temperature function is determined by computing a best fit to the frequency—temperature data. A function of the form:

$$f_r = f_m * (1 + (T_m - T_r)/C)$$

where: $f_r$ is the resonant frequency compensated to the reference temperature, $f_m$ is the measured resonant frequency, $T_m$ is the measured temperature and $T_r$ is the reference temperature, and C is a constant determined by the best fit and referred to as the temperature compensation factor; has been found to be a good general form. However, any suitable mathematical function using these terms can be used.

The second step is to measure the temperature of the remainder of the parts or specimens as the resonant frequencies are measured. The temperature function is then used to adjust the measured frequency to the frequency at the reference temperature. The temperature function can be computed and applied manually, but the preferred embodiment is to provide it in the operating system of the instrument used to make the frequency measurement. The temperature of the object can be measured either by contact or using a remote sensor. Directly contacting the object while the frequency is being measured, can affect the frequency measurement. So if direct contact is used, it is best to measure the temperature of the object immediately before its resonant frequencies are measured. Alternately, a surrogate part can be used for the temperature measurement. The surrogate is a part of the same type, which has been stored or handled in such a way that it is at essentially the same temperature as the part (or parts) being measured. Then the temperature probe can be attached to the surrogate part with the knowledge that it will be reading the same temperature as the temperature of the object whose resonant frequency is being measured. This allows quick, accurate temperature measurements without the need to repeatedly attach and remove a temperature probe.

In some cases the temperature function measured for each resonance may be unique. In practice, it has been found that the functional relationships for an object's resonances are similar enough that averaging can be used to compute a single temperature function that can be applied to all of the resonances of interest for a given part with acceptable accuracy. In practicing this invention, one is cautioned to experimentally determine whether a temperature function is acceptable for a given part measurement.

The third step is to apply the appropriate resonant techniques for defect detection or materials evaluation using the measured resonant frequencies compensated to the reference temperature.

FIG. 1 illustrates temperature compensation in accordance with the method of this application. The top curve in FIG. 1, labeled temp 23, shows a resonant frequency measurement of a part at 23° C. The horizontal axis is frequency in KHz and the vertical axis is amplitude of the vibration. The resonant frequency is 68.4 kHz which is indicated by the vertical cursor and printed to the right of the trace. The second trace, labeled temp 31, in FIG. 1, shows a resonant frequency measurement measured at a temperature of 31° C. Here, the RUS measurement is shifted slightly, to 68.318 KHz because of the higher temperature. The third curve, labeled comp 23, shows the effect of using the temperature function to compensate the measurement back to 23° C. Here, the compensated frequency is 68.397 KHZ, which is close to the true frequency of 68.400 KHz. The error of 0.003 KHz is caused by the fact that the temperature function determined by computing a best fit to the frequency-temperature data is not perfect.

What is claimed:

1. A method of compensating resonant frequency measurements for the effects of variation in temperature of a measured object comprising the steps of:

exciting a metallic or ceramic manufactured part with a transducer to obtain resonant responses;

measuring frequency of selected resonances of the metallic or ceramic manufactured part at a reference temperature;

heating or cooling the part or specimen to another temperature and measuring the new temperature;

measuring the frequency of the selected resonances at the new temperature, repeating the measurements of frequency and temperature for several temperatures;

determining a temperature function which is a mathematical relationship between each resonant frequency and temperature; and using the temperature function to adjust the frequencies measured (fm) at any temperature (Tm) to the frequency (fr) at the reference temperature (Tr).

2. A method in accordance with claim 1, in which the temperature function for a measured object is determined by averaging temperature functions for several selected resonances.

3. A method in accordance with claim 2 in which the method of frequency measurement applies a frequency to a part, measures the response and then steps to a next frequency across a predefined frequency.

4. A method in accordance with claim 1, in which temperature of a surrogate part or specimen is measured to eliminate a need to touch a part being tested, wherein said surrogate part or specimen is of the same type and has essentially the same dimensions and material properties as the part being tested and is positioned and mounted such that its temperature is essentially the same as the part being tested.

5. A method in accordance with claim 4 in which the method of frequency measurement applies a frequency to a part, measures the response and then steps to a next frequency across a predefined frequency.

6. A method in accordance with claim 1, in which the temperature of the part is periodically read by a sensor and part temperature is input to the temperature function to compensate the part or specimen being tested for temperature change.

7. A method in accordance with claim 6 in which the method of frequency measurement applies a frequency to a part, measures the response and then steps to a next frequency across a predefined frequency.

8. A method in accordance with claim 1, in which a temperature sensor directly contacts the part or specimen before the frequency is measured.

9. A method in accordance with claim 8 in which the method of frequency measurement applies a frequency to a part, measures the response and then steps to a next frequency across a predefined frequency.

10. A method in accordance with claim 1, in which temperature is remotely sensed with an infrared sensor.

11. A method in accordance with claim 10 in which the method of frequency measurement applies a frequency to a part, measures the response and then steps to a next frequency across a predefined frequency.

12. A method in accordance with claim 1, in which the temperature function is of the form $f_r=F(f_m, T_m, T_r)$ where $f_r$ is the resonant frequency compensated to the reference temperature, $f_m$ is the measured resonant frequency, $T_m$ is the measured temperature and $T_r$ is the reference temperature and F is the mathematical notation for "any function of".

13. A method in accordance with claim 12 in which the method of frequency measurement applies a frequency to a part, measures the response and then steps to a next frequency across a predefined frequency.

14. A method in accordance with claim 1 in which the method of frequency measurement applies a frequency to a part, measures the response and then steps to a next frequency across a predefined frequency.

15. A method of compensating resonant frequency measurements for the effects of variation in temperature of a measured object comprising the steps of:
  exciting a metallic or ceramic manufactured part with a transducer to obtain resonant responses;
  measuring frequency of selected resonances of metallic or ceramic the manufactured part at a reference temperature;
  heating or cooling the part or specimen to another temperature and measuring the new temperature;
  measuring the frequency of the selected resonances at the new temperature, repeating the measurements of frequency and temperature for several temperatures;
  determining a temperature function which is a mathematical relationship between each resonant frequency and temperature; and
  using the temperature function to adjust the frequencies measured (fm) at any temperature (Tm) to the frequency (fr) at the reference temperature (Tr) wherein the temperature function is of the form: $f_r=f_m*(1+(T_m-T_r)/C)$ where $f_r$ is the resonant frequency compensated to the reference temperature $f_m$ is the measured resonant frequency, $T_m$ is the measured temperature and $T_r$ is the reference temperature.

16. A method in accordance with claim 15 in which the method of frequency measurement applies a frequency to a part, measures the response and then steps to a next frequency across a predefined frequency.

17. A method for compensating the measured resonant frequency of metallic or ceramic manufactured parts whose temperature is varying with time, wherein analytical methods developed at a baseline temperature are applied to determine whether the parts are defective comprising the steps of:
  exciting the metallic or ceramic manufactured part with a transducer to obtain resonant response;
  determining at least one mathematical temperature compensation function for a specific part sample which is known to be free of defects by;
    measuring at least one response resonant frequency while the part is at a known baseline temperature,
    heating or cooling the part to a series of different temperatures,
    repeating the resonant response frequency measurement at said different temperatures, and
    fitting a relationship between baseline temperature and the different temperatures to an appropriate mathematical formula;
  measuring temperature of a part of unknown quality as its resonant frequencies are applied;
  applying at least one mathematical temperature compensation function to the measured resonant frequencies of the part of unknown quality to convert the measured resonant frequencies to the value they would have at the baseline temperature; and
  applying analytical techniques to the compensated resonant frequency data to determine whether the part is good or defective.

* * * * *